(12) United States Patent
Evers (10) Patent No.: US 8,569,713 B2
(45) Date of Patent: Oct. 29, 2013

(54) RADIONUCLIDE GENERATOR AND METHOD OF STERILIZATION

(75) Inventor: John Henry Evers, Medway, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

(21) Appl. No.: 13/320,216

(22) PCT Filed: May 13, 2009

(86) PCT No.: PCT/US2009/002998
§ 371 (c)(1),
(2), (4) Date: Feb. 21, 2012

(87) PCT Pub. No.: WO2010/132043
PCT Pub. Date: Nov. 18, 2010

(65) Prior Publication Data
US 2012/0187308 A1    Jul. 26, 2012

(51) Int. Cl.
*G21G 4/04* (2006.01)
*G21G 4/08* (2006.01)
*G21G 4/06* (2006.01)

(52) U.S. Cl.
CPC ... *G21G 4/04* (2013.01); *G21G 4/06* (2013.01)
USPC ............... 250/438; 250/428; 250/432 PD; 250/432 R; 250/505.1; 250/506.1

(58) Field of Classification Search
CPC ......... G21G 1/0005; G21G 4/04; G21G 4/06; G21G 4/08; G21H 5/00; G01M 21/24
USPC ............ 250/428, 432 PD, 432 R, 438, 505.1, 250/506.1
See application file for complete search history.

(56) References Cited

U.S. PATENT DOCUMENTS

| | | |
|---|---|---|
| 3,382,152 A | 5/1968 | Lieberman et al. |
| 3,446,965 A | 5/1969 | Ogier et al. |
| 3,535,085 A | 10/1970 | Shumate et al. |
| 3,576,998 A | 5/1971 | Deutsch et al. |
| 3,655,981 A | 4/1972 | Montgomery et al. |

(Continued)

FOREIGN PATENT DOCUMENTS

JP    54-101094 A    8/1979

OTHER PUBLICATIONS

Molinski, A Review of 99M Tc Generator Technology. Int. J. Appl. Radiat. Isot. 1982;33:811-9.

(Continued)

*Primary Examiner* — David A Vanore
(74) *Attorney, Agent, or Firm* — Wolf, Greenfield & Sacks, P.C.

(57) ABSTRACT

A column assembly of a radionuclide generator includes a column that retains a parent radionuclide that spontaneouosly decays to a relatively short-lived daughter radionuclide. A fluid path extends from an inlet port to the column and then to an outlet port and allows daughter radionuclide to be eluted from the radionuclide generator for use. Improved retention of parent radionuclide in the column is accomplished by preventing fluid from entering the flow path in a liquid state, such as during sterilization. Proper column chemistry is also promoted by preventing excess moisture from coalescing in the column, which may promote a higher and/or more reliable yield of daughter radionuclide from a radionuclide generator.

20 Claims, 8 Drawing Sheets

(56) References Cited

U.S. PATENT DOCUMENTS

| | | | |
|---|---|---|---|
| 3,774,035 A * | 11/1973 | Litt ............................... | 252/645 |
| 3,920,995 A * | 11/1975 | Czaplinski et al. ....... | 250/432 R |
| 4,239,970 A * | 12/1980 | Eckhardt et al. ........ | 250/432 PD |
| 4,666,676 A * | 5/1987 | Nelson et al. ................ | 422/149 |
| 5,109,160 A * | 4/1992 | Evers ..................... | 250/432 PD |
| 6,157,036 A * | 12/2000 | Whiting et al. ......... | 250/432 PD |
| 7,091,494 B2 * | 8/2006 | Weisner et al. ......... | 250/432 PD |
| 7,700,926 B2 * | 4/2010 | Tartaglia et al. ........ | 250/432 PD |
| 7,998,106 B2 * | 8/2011 | Thorne et al. .................. | 604/32 |
| 8,058,632 B2 * | 11/2011 | Balestracci et al. ....... | 250/507.1 |
| 2005/0253085 A1 | 11/2005 | Weisner et al. | |
| 2008/0073559 A1 * | 3/2008 | Horsky et al. ................ | 250/428 |
| 2008/0191148 A1 | 8/2008 | Gibson | |
| 2012/0187308 A1 * | 7/2012 | Evers ..................... | 250/432 PD |

OTHER PUBLICATIONS

Steigman, Chemistry of the Alumina Column. Int. J. Appl. Radiat. Isot. 1982;33:829-34.

Vucina, Elution Efficiency of MO-99/Tc-99M Generators. Facia Universitatis. 2001;2(3):125-30.

* cited by examiner

RADIONUCLIDE GENERATOR AND METHOD OF STERILIZATION

RELATED APPLICATIONS

This application is a national stage filing under 35 U.S.C. §371 of International Application No. PCT/US2009/002998, filed May 13, 2009, which was published under PCT Article 21(2) in English, the entire contents of which are incorporated by reference herein.

BACKGROUND

1. Field

Aspects of the present invention relate to a radionuclide generator having a column assembly that may be terminally sterilized without the introduction of excess moisture.

2. Discussion of Related Art

Radionuclide generators include a column that has media for retaining a long-lived parent radionuclide that spontaneously decays into a daughter radionuclide that has a relatively short-lived life. The column may be incorporated into a column assembly that has a needle-like outlet port that receives an evacuated vial to draw saline or other eluant liquid, provided to a needle-like inlet port, through a flow path of the column assembly, including the column itself. This liquid may elute and deliver daughter radionuclide from the column and to the evacuated vial for subsequent use in nuclear medical imaging applications, among other uses. One example of a generator is shown and described in U.S. Pat. No. 5,109,160, owned by Lantheus Medical Imaging, Inc., and which is incorporated by reference herein in its entirety.

Sterilization to some degree is generally performed on radionuclide generators that are used in the medical industry. Sterilization may be performed by exposing a column assembly of a radionuclide generator, having a column loaded with parent radionuclide, to a saturated steam environment. During this process, liquid that resides in the column assembly, including the column and tubes that extend between the column and the inlet and outlet ports may be heated to vapor form (e.g., steam) to kill and/or inactivate contaminants. A vent may be included at the outlet port to allow both the introduction of steam and the release of vapors from the column during the sterilization process.

As discussed in U.S. Pat. No. 5,109,160, it may be desirable to provide a radionuclide generator as a terminally sterile product—that is, a product that is sterilized in its final container, or at least that is sterilized with the flow path between the inlet port, the column, and the outlet port assembled in its final form, including any vented or non-vented caps over the inlet and outlet ports. This may be contrasted with aseptic sterilization where at least some of the individual components that make up the flow path between the inlet port, the column, and the outlet port are sterilized separately and subsequently assembled together.

SUMMARY

Providing a vented outlet cover at the outlet port of a column assembly during sterilization, instead of assembling a cap or cover after sterilization, may help a product achieve terminal sterilization. The applicant has discovered, however, that vented outlet covers may, in some instances, provide an entranceway to the flow path of a column assembly for unwanted liquid, despite the presence of a filter at the vent opening of a vented outlet cover. In fact, the applicant observed that a filter on a upwardly facing vent opening has provided a surface on which condensate may accumulate during or after steam sterilization. The accumulated condensate was found to breach the filter and enter the column assembly flow path, in some cases, and to be the cause of reductions in product life (i.e., elution efficiency) and in radioactive integrity (i.e., column assemblies emitting an amount of radiation that exceeds a threshold level), prior to product shipment. These reductions, until the present invention, were unexplained for years.

According to one aspect, a column assembly of a radionuclide generator includes a column having an interior containing a medium for retaining a long-lived parent radionuclide that produces a relatively short-lived daughter radionuclide. The column assembly includes an inlet port in fluid communication with the interior of the column and an outlet port in fluid communication with the interior of the column. The column assembly includes a vent opening that provides fluid access to the interior of the column via the outlet port. The vent opening is configured to provide fluid access and to prevent condensate from entering the vent opening or outlet port.

According to another aspect, a method is provided for producing a terminally sterile column assembly of a radionuclide generator. The method comprises providing a column assembly of a radionuclide generator that includes a column having a long-lived parent radionuclide that produces a relatively short-lived daughter radionuclide. The column assembly also includes an inlet port in fluid communication with the column and an outlet port in fluid communication with the column. The outlet port includes a vent opening that provides fluid access to the column. The column assembly is positioned in an orientation with the vent opening facing downwardly to prevent condensate from entering the vent from above. The column assembly is also exposed to steam for sterilization.

According to at least some embodiments, an outlet cover at least partially covers the outlet port and includes the vent opening. The outlet port may include a needle structure and the outlet cover may include a pierceable membrane that receives the needle structure of the outlet port. In some embodiments, the outlet cover includes a body portion and a removable cap. The vent opening may be defined as an annular space between the removable cap and the body portion.

According to some embodiments, a filter is in the outlet cover. The filter may be bacteria retentive, according to some embodiments. The filter may be positioned at the vent opening.

According to some embodiments, a filter may be positioned between and in fluid communication with the outlet port and the column.

In some embodiments, the inlet port may be accessible from outside of a shielded package that receives the column assembly, when the column is inside of the shielded package. The column assembly may be provided in combination with the shielded package.

A plug may be removably attached to the inlet port to block fluid communication to the inlet port from an atmosphere outside of the column assembly, according to some embodiments.

The medium in the column may include alumina, according to some embodiments.

The column assembly may be provided in combination with the long-lived parent radionuclide and the relatively short-lived daughter radionuclide, according to some embodiments, and the long-lived parent nuclide may include molybdenum-99 and the relatively short-lived daughter radionuclide may include technetium-99m.

According to some embodiments, a plurality of column assemblies may be exposed to a steam environment at a common time for one or more sterilization cycles. In some embodiments, exposing the plurality of column assemblies to steam for a single sterilization cycle results in an amount of remaining liquid that varies by 5% or less (relative standard deviation). In other embodiments, exposing the plurality of column assemblies to steam for two sterilization cycles results in an amount of remaining liquid that varies by 15% or less (relative standard deviation).

According to another aspect, a column assembly of a radionuclide generator is provided that includes a column and an outlet port. The column has a medium for retaining a long-lived parent radionuclide that produces a relatively short-lived daughter radionuclide. The outlet port is in fluid communication with the column and is covered with a vented outlet cover to provide a terminally sterilizable column assembly. The vented outlet cover has a vent opening that provides fluid access to the column and that to prevents the ingress of gravity-driven liquid (condensate) to produce a column assembly that consistently exhibits high yield and that prevents migration of parent radionuclide away from the column.

According to another aspect, a column assembly of a radionuclide generator includes a column and an outlet port. The column has a medium for retaining a long-lived parent radionuclide that produces a relatively short-lived daughter radionuclide. The outlet port is in fluid communication with the column and is covered with a vented outlet cover to provide a terminally sterilizable column assembly. Means are provided to prevent the ingress of gravity-driven liquid to produce a column assembly that consistently exhibits high yield and that prevents migration of parent radionuclide away from the column.

According to some embodiments, the means comprises a vent opening that provides fluid access to the column and that prevents the ingress of gravity-driven liquid. The vent opening may face toward the column, according to some embodiments.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Broadly speaking, a radionuclide generator includes a column that retains a parent radionuclide which spontaneously decays to a relatively short-lived daughter radionuclide. The column may be incorporated into a column assembly that includes a fluid path extending from an inlet port, through the column, and then to an outlet port from which daughter radionuclide may be delivered for use. The column assembly is typically positioned within a shielded package. Some aspects described herein provide for improved retention of parent radionuclide in the column where radioactive shielding is typically the greatest. This may be accomplished by venting a column assembly in a manner that prevents the ingress of liquids during sterilization, yet that allows for the exchange of steam and/or other vapors. This, in turn, may reliably prevent excess liquid from being introduced to portions of the column assembly, such as portions of the inlet and outlet tubes where the presence of excess liquid might provide a pathway for unwanted migration of radionuclide. Other aspects of the invention relate to reliably preventing excess moisture from coalescing in or about the column, which may adversely impact column chemistry and lead to reduced yield of daughter radionuclide.

Parent radionuclide is typically provided to a column in a fluid charge, where the radionuclide selectively binds to media in the column while the fluid charge is drawn through the column along a flow path of a column assembly. During sterilization there is an exchange of vapors, through the vented outlet cover, between heated, residual charging fluid residing in the column assembly flow path and the saturated steam present in a sterilization chamber. During the cooling process that follows sterilization, steam may condense about a column assembly and may enter the column assembly, as liquid, through an outlet port (absent features to prevent the ingress of gravity-driven liquid), resulting in excess liquid in the column assembly flow path. Excess liquid that may reside in the column or other portions of the flow path between the inlet port and outlet port of a radionuclide generator column assembly may provide a path along which parent radionuclide may migrate. Migration, in some instances, may occur to areas of a flow path that are shielded to a lesser degree than the column itself, which may result in radiation being emitted at a level that exceeds a threshold level. Aspects of the invention described herein relate to controlling the moisture content of a column assembly during and/or after steam sterilization so as to prevent excess liquid in the flow path of a column assembly, along which radionuclide may migrate.

Excess moisture in the column or column assembly of a radionuclide generator may result from the entry of liquid into the column assembly during or after steam sterilization, and may adversely impact column chemistry, resulting in reduced yield of daughter radionuclide. Aspects of the invention relate to controlling the amount and/or phase state of moisture that may enter a column during or after sterilization to promote the production of a high yield radionuclide generator.

It many instances, it may be desirable to provide a radionuclide generator that is terminally sterile. This involves sterilizing the column assembly, including the flow path between inlet port, column, and the outlet port, and any plugs or vented covers positioned on the inlet and outlet ports, when assembled together in final form, at least prior to being installed in a shielded container. Aspects of the invention relate to providing a terminally sterile product, including sterilization after fully assembling any plugs and vented covers to the flow path, while also reliably controlling the amount of moisture in the flow path of the column assembly.

Figure 1:
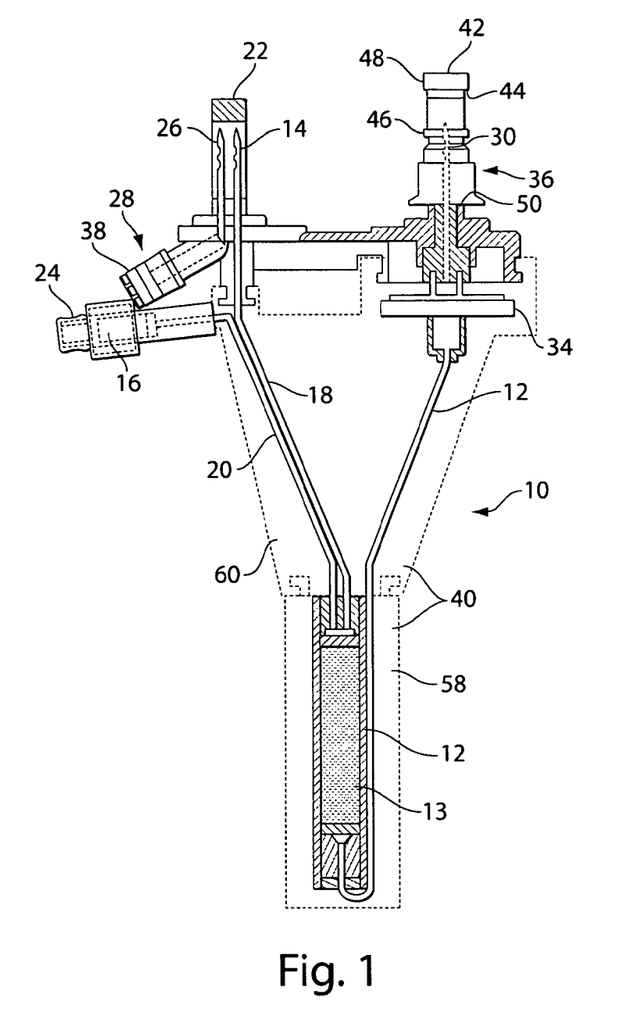
FIG. 1 is a cross sectional view of a column assembly, according to one embodiment, that includes a flow path extending from an inlet port covered with a plug, through a column, and to an outlet port covered with an outlet cover having a vent configured to prevent the ingress of liquid.

Turning now to the Figures, and initially FIG. 1, one embodiment of a column assembly 10 of a radionuclide generator is shown. The column assembly 10 includes a column 12 having a media 13 and that is fluidly connected at one end to an inlet port 14 and a charge port 16 through an inlet line 18 and a charge line 20, respectively. As shown, the inlet port 14 and charge port 16 are each covered with a plug 22, 24. A vent port 26 that communications fluidly with an eluant vent 28 is positioned adjacent to the inlet port 14, and may, in operation, provide a vent to a vial or bottle of eluant connected to the inlet port, as described in greater detail herein.

The column assembly 10 also includes an outlet port 30 that is fluidly connected to the bottom of the column 12 through an outlet line 32. A filter assembly 34 is incorporated into the outlet line, and the outlet port 30 is covered with a vented outlet cover 36 that also includes a filter, as described in greater detail below. Various aspects of the illustrated embodiment of the column assembly are described in greater detail in U.S. Pat. No. 5,109,610 (Evers), owned by Lantheus Medical Imaging, Inc, which is hereby incorporated by reference in its entirety. Additionally, column construction materials and operation are described in U.S. Pat. No. 3,476,998 (Deutsch) and U.S. Pat. No. 3,774,035 (Litt), each of which is also hereby incorporated by reference in its entirety.

Manufacture of a radionuclide generator, according to some embodiments, includes charging the column with a parent radionuclide after the column assembly has been assembled. This may be accomplished by providing a vial or bottle that includes a parent radionuclide, such as molybdenum-99 (Mo-99) in solution, to the charge port 16. The Mo-99 in solution is then drawn to the column, either by applying a vacuum at the outlet port 30 or by driving the fluid to the column under pressure provided at the charge port 16. The parent radionuclide in solution passes through a medium 13 in the column, such as alumina, that has an affinity for and that retains parent radionuclide therein. It is to be appreciated that embodiments of the column assembly may be charged with parent radionuclide other than molybdenum-99 (which produces technetium-99m as a daughter radionuclide). By way of non-limiting example, column assemblies may be charged with germanuim-68 as a parent radionuclide to produce gallium-68 as a daughter radionuclide or with tungsten-188 as a parent radionuclide to produce rhenium-188 as a daughter radionuclide.

Figure 2:
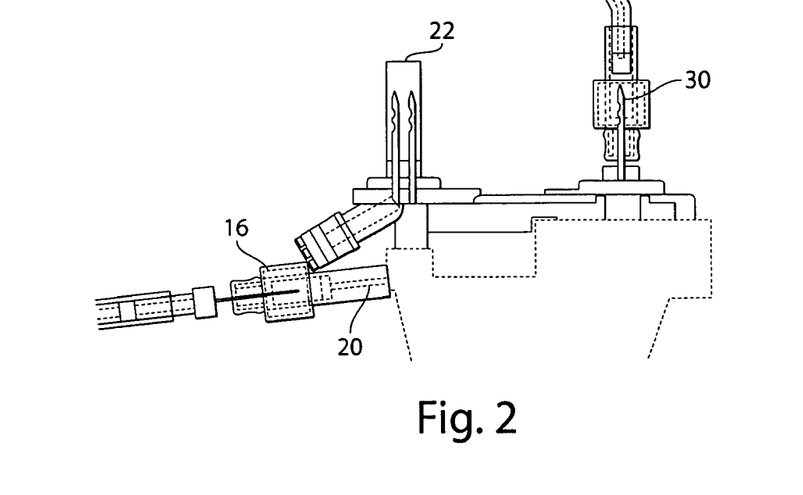
FIG. 2 shows portions of the column assembly of FIG. 1, configured for charging of the column with parent radionuclide.

FIG. 2 illustrates portions of a column assembly configured for charging the column with parent radionuclide. Having a charge line 20 and charge port 16 that are separate from the inlet line 18 and inlet port 14 (as shown in FIG. 1), which are typically plugged as the column 12 is charged, may prevent radionuclide from entering the inlet line 18 of the column assembly 10. A plug 24, which may be permanent, may be placed over the charge port 16 after charging the column to prevent migration of radionuclide back up the charge line 20 from the column. After charging, a vented outlet cover 36 may be positioned over the outlet port 30 (as shown in FIG. 1). Other plugs and features, including a vent cap 38 positioned over the eluant vent 28, may be assembled to the column assembly 10 prior to or after charging the column to ready the device for sterilization.

Figure 4:
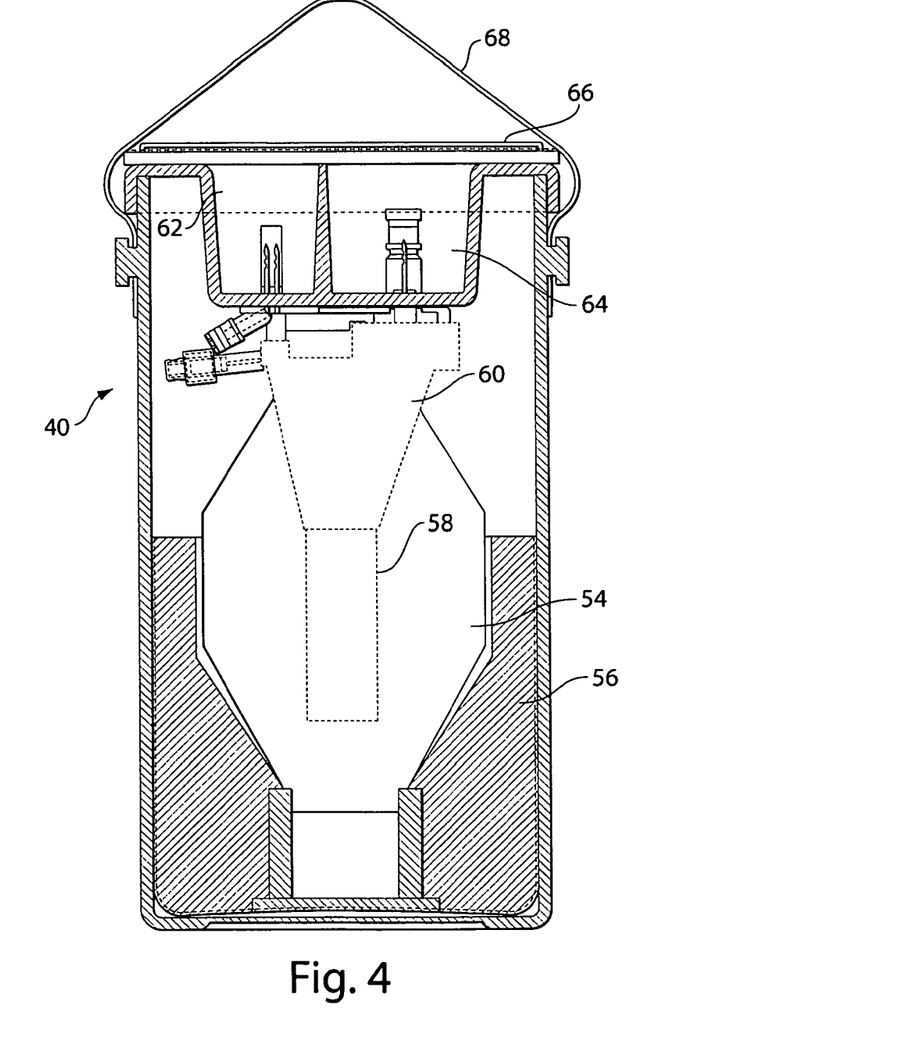
FIG. 4 is a cross sectional view of the column assembly shown in FIG. 1, assembled into a shielded package.

The flow path of the column assembly 10, including the inlet port 14, inlet line 18, column 12, outlet line 32, and outlet port 30, among other features, may be sterilized with the inlet plug 22 and vented outlet cover 36 in position, and prior to the column assembly being placed in a shielded package 40 (as shown in FIG. 4). Sterilization of the column assembly in this manner may provide for a terminally sterile column assembly, given that no further manipulations of customer access points (i.e., the inlet port and the outlet port) or internal portions of the flow path therebetween may be performed subsequent to sterilization and prior to the radionuclide generator being accessed by an end user. Alternatively, the column assembly may merely be assembled into a shielded package to complete assembly of a radionuclide generator, as discussed in greater detail herein, and readied for shipment.

According to some embodiments, sterilization includes exposing the column assembly 10 to a saturated steam environment. This may involve placing one or more column assemblies into a sterilization chamber, each assembly having a plug 22 positioned over the inlet port and optionally over the vent port 26, and a vented outlet cover 36 positioned over the outlet port 30. Steam is provided to the sterilization chamber as the pressure of the chamber is increased until a desired temperature and pressure are achieved. According to some embodiments, column assemblies are exposed to a saturated steam environment at a pressure higher than atmospheric. It is to be appreciated that sterilization may involve various combinations of temperature and pressure values, such as combinations of pressure and temperature associated with a saturated steam environment, as may be determined from a psychrometric chart, and that types of sterilization other than saturated steam may also be used, as the embodiments are not limited to the sterilization techniques described herein. Additionally, different combinations of plugs and/or vented covers may be positioned over the inlet, outlet, and/or other access points, and in some embodiments, access points may be uncovered during sterilization.

A column assembly may be oriented during sterilization to help retain radionuclide activity within the column and/or portions of the flow path near the column.

According to some embodiments, the column assembly 10 may be oriented in a similar way, typically with the column assembly lower than other portions of the flow path, both during sterilization and when placed in a shielded package 40 for delivery and/or use. As shown in the embodiment of FIG. 1, the column 12 may be positioned near a lower portion of a column assembly 10, such that any liquid within the system is directed by gravity toward the column or portions of the flow path that are near the column, where shielding of a shielded package is generally thicker. The inlet and outlet lines 18, 32 may be oriented substantially vertically or diagonally downward at all points, lacking dips or horizontal sections that might otherwise trap liquid containing radionuclide after charging, elution, and/or during sterilization. It is to be appreciated that the embodiment of FIG. 1 shows but one configuration of inlet and outlet lines, and other others are also possible, including for instance lines that are configured differently from that shown in FIG. 1, but that are generally ramped downward toward an area near the column at all points along their length.

During steam sterilization, residual fluid used in charging the column with radionuclide is heated to a vapor form (e.g., steam) to kill and/or inactivate contaminants. The vapor may be driven at least partially from the column assembly while steam also enters the column assembly from the saturated steam environment within the sterilization chamber, such that there may be minimal or no net change in moisture content of a column assembly during sterilization. At least one vent opening, typically positioned at the outlet port, and that may optionally include a filter, may be left open between the column and the steam environment during the sterilization process to allow for the ingress and egress of steam to the column. Although moisture exchange occurs between the flow path of the column assembly, including the column itself, and the environment during sterilization, no net change or a minimal net change in the amount of moisture in the column assembly may generally be desirable.

Figure 3:
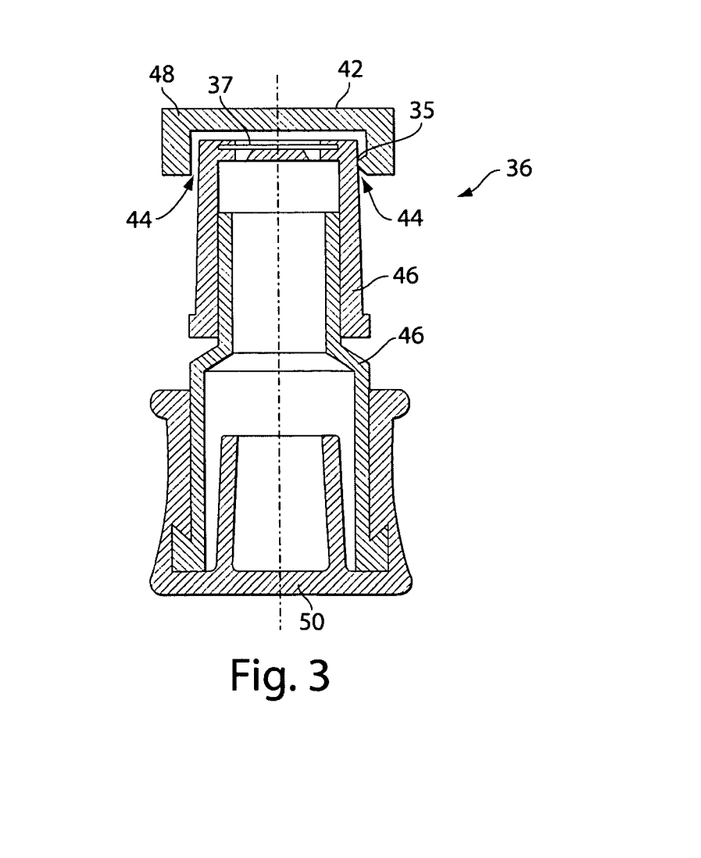
FIG. 3 is a cross sectional view of a vented outlet cover with a vent opening oriented to prevent the ingress of liquid from above, according to one embodiment.

Condensation may occur as the environment about the column assembly cools to room temperature and/or returns to atmospheric pressure after sterilization. Such condensation may collect on surfaces of the column assembly, and particularly horizontal surfaces, such as the top 42 of the vented outlet cover 36 (or equivalently the filter 37 of vented outlet cover 36, absent cap 48 and top surface 42 as shown in FIG. 3). Additionally or alternatively, particular positions within a sterilization chamber may be more prone to the production of condensation, due to air flow within the chamber, or by virtue of being positioned under features from which condensate may drip, among other factors. The applicant has appreciated that while the flow of saturated steam both to and from the flow path of a column assembly may prove beneficial in the sterilization process, that the introduction of fluid in a liquid state, such as condensate, to the flow path during or after sterilization may not be desirable. Steam or fluid in vapor form may naturally flow to and from the flow path of a column assembly at equivalent rates and/or equivalent amounts, such that there is minimal or no net change in moisture content of a column assembly during sterilization. On the other hand, fluid that may enter the flow path of a column in liquid form, particularly after the sterilization process, may not find a way back to the external environment, resulting in a net gain of moisture content in a column assembly subsequent to sterilization.

Embodiments of the vented outlet cover 36 may include one or more features to prevent the ingress of fluid in liquid form, while allowing the ingress and egress of fluid in a vapor form (e.g., steam). In one illustrative embodiment shown in FIG. 3, the cover 36 includes a vent opening 44 that faces substantially downwardly, such that condensate, when driven by gravity, will not enter the vent opening 44, but instead be shed downward toward lower, external portions of the column assembly or away from the column assembly 10 altogether. It is to be appreciated that the term "downwardly" as used herein with respect to a column assembly refers to a direction in which the pull of gravity draws a mass in relation to a column assembly that is oriented for use. In the illustrated embodiment, the vent opening 44 has an annular shape that is defined between a body portion 46 of the cover and a removable cap 48 positioned on the body portion. The cap 48 includes a liquid impermeable top surface 42 that is positioned above the vent opening 44, when assembled, and prevents water from entering the vent from above. Components of the vented outlet cover represented by FIG. 3 may be acquired from Filtertek, Inc. of Hebron, Ill. is to be appreciated that FIG. 3 shows one embodiment of a vented outlet cover, and that other embodiments are also possible. By way of example, the vented outlet cover may include a vent opening that is oriented to prevent water from entering the vent without the vent opening facing directly downward. According to some embodiments, the vent opening may be oriented to face substantially sideways and still prevent liquid from entering the vent opening, and the flow pathway of a column assembly. It is to be appreciated that the term "vent opening" or equivalently "vent", as used herein, refers to a space or opening delimited by portions of the column assembly and through which steam may pass from an environment external to the column assembly, through the outlet port, and into the interior of a column assembly.

Whether an upward facing vent opening of a column assembly is exposed to liquid during sterilization may be a result of the column assembly being positioned in particular places within a sterilizer and/or by chance, as one of skill in the art is to appreciate. In this respect, it is possible that column assemblies with upwardly facing vent openings may be sterilized without the introduction of excess liquid. The introduction of liquid to such column assemblies, however, may prove to be unpredictable. In contrast, column assemblies having vent openings facing downwardly may prevent or reduce the introduction of liquid and/or excessive moisture into the column. According to some embodiments, the liquid content amongst a plurality of column assemblies, after a single sterilization cycle, may vary as measured in standard deviation by fewer than 0.015 grams, fewer than 0.010 grams, fewer than 0.005 grams, or by an even lesser amount. According to some embodiments, column assemblies with an average of 0.040 grams of liquid may vary in liquid content by 0.002 grams or fewer (standard deviation) after a single sterilization cycle. Similarly, the liquid content may vary by less than 40%, less than 30%, less than 20%, less than 10%, less than 5%, less than 4%, less than 3%, less than 2%, or even less than 1%, as measured in relative standard deviation, after a single sterilization cycle. These reductions in standard deviation and relative standard deviation may represent greater than a 25% reduction, a 50% reduction, a 75% reduction, or even greater than a 90% reduction as compared to column assemblies that lack vent openings that face downwardly (e.g., that have vent openings facing upwardly). The liquid content amongst the same plurality of column assemblies, after a second sterilization cycle, may vary as measured in standard deviation by fewer than 0.100 grams, fewer than 0.050 grams, fewer than 0.010 grams, or by an even lesser amount. In some embodiments, column assemblies with an average of 0.039 grams of liquid may vary in liquid content by 0.006 grams or fewer (standard deviation) after two sterilization cycles. Similarly, the liquid content may vary by less than 200%, less than 100%, less than 50%, less than 15%, less than 10%, less than 5%, less than 4%, less than 3%, less than 2%, or even less than 1%, as measured in relative standard deviation, after two sterilization cycles. These reductions in standard deviation and relative standard deviation may represent greater than a 25% reduction, a 50% reduction, a 75% reduction, or even greater than a 90% reduction as compared to column assemblies that lack vent openings that face downwardly (e.g., that have vent openings facing upwardly).

The cap 48 of the vented outlet cover shown in FIG. 3 is configured to be removable from the body portion 46 of the vented outlet cover. As shown, the cap 48 includes tabs 35 that mate with corresponding features of the body portion 46 to hold the cap in place. Removable caps may be configured to mate to other portions of the vented outlet cover in other ways, such as with threaded connections, press fit connections, and the like, according to some embodiments. According to other embodiments, the vented outlet cover may lack a removable cap while still having a vent opening that faces substantially downward.

The outlet port, according to some embodiments, may additionally or alternatively be configured to prevent the ingress of gravity-driven liquid, such as condensate, when a column assembly is oriented with a column positioned lower than the outlet port for sterilization, shipment, and/or use. By way of example, according to some embodiments, the outlet port itself may act as a vent opening and face substantially downwardly, such that gravity-driven liquid may not enter the vent opening from above. Such embodiments may be sterilized without a vented outlet cover assembled to the column assembly, and may additionally be shipped for use without a vented outlet cover.

The vented outlet cover 36 may connect to the outlet port 30 in different manners. In the embodiment of FIG. 1, the outlet port 30 includes a needle-like structure, and the vented outlet cover 36 includes a pierceable membrane 50 (as shown in FIG. 3) that may receive the needle-like structure to provide a seal therebetween and to retain the outlet cover in place. Other types of connections, however, are also possible, including screw type connections and/or press type fit connections, to name a few.

Filters may be incorporated into the flow path of a column assembly, according to some embodiments. The embodiment of FIG. 1 includes a filter 34 assembly positioned in the outlet line 32 to prevent the egress of particulates from the column and to maintain sterility of the radionuclide generator eluate. Similar filters may additionally or alternatively be positioned elsewhere in the flow path of a column assembly. For example, a filter 37 may be positioned within a vented outlet cover 36, as shown in FIG. 3, or even directly at the opening of the vent, according to some embodiments. The filter may include a glass matrix sandwiched between cellulose layers that hold the glass matrix in place, and may be configured to retain bacteria, rather than solely preventing bacteria passage.

The column assembly 10 may be positioned in a package 40 that includes shielding to prevent the emission of radiation from the column assembly above a threshold value. By way of example, FIG. 4 shows the column assembly 10 of FIG. 1 assembled into a package 40 that has a lead shield base 54 or shield of other suitable material, such as tungsten or depleted uranium, held in position by a spacer 56. The package receives the column assembly with a column shield 58 positioned around the column 12 and a shield plug 60 positioned about portions of the inlet and outlet lines of the flow path. As may be appreciated, the thickest and thus greatest amount of shielding may typically exist around the column 12, where radionuclide is expected to reside. The inlet and outlet lines 18, 32 are also shielded, but to a lesser degree. The package 40 additionally includes a charge well 62 about the inlet port 14 and the vent port 26 where an eluant bottle may be received when daughter radionuclide are to be eluted. The package may also include a collection well 64 about the outlet port 30 that may be accessed by a shielded, evacuated vial or other container when radionuclide are retrieved from the column assembly 10, as discussed in greater detail herein. A dust cover 66 may be removably positioned over the charge well 62 and collection well 64, and the package may include a handle 68, as shown in FIG. 4.

Embodiments of column assemblies may be configured to prevent radiation emission from exceeding different threshold levels, according to varying criteria. By way of non-limiting example, according to some embodiments, a common threshold level may be defined for column assemblies, regardless of a charge level, as measured in Curies, of a radionuclide generator. According to one embodiment, a threshold limit of 200 mR/hr may be set as a threshold limit, as measured outside of a square corrugated carton having side edges of about 14" in length and that encloses a column assembly positioned inside of a shielded package. Other values of threshold limits may alternatively be set, such as at lower threshold limits as the embodiments described herein are not limited to any one threshold value. According to other embodiments, threshold limits may depend on the degree to which a column assembly is charged with parent radionuclide. Some examples of threshold levels associated with different charge levels, are shown below in Table 1.

TABLE 1

Examples of Threshold Limits

| Charge Level (mCi) | Threshold Limit (mR/hr) |
|---|---|
| 1000 | 27 |
| 2000 | 41 |
| 2500 | 46 |
| 3000 | 36 |
| 4000 | 46 |
| 4500 | 50 |
| 5000 | 54 |
| 6000 | 63 |
| 7500 | 76 |
| 10000 | 98 |
| 12500 | 121 |
| 15000 | 140 |
| 18000 | 159 |

To retrieve daughter radionuclide from the generator, the dust cover 66 is first removed, and then the inlet port plug 22 is removed from the inlet port 14 and vent port 26. The vented outlet cover 36 is also removed from the outlet port 30. A bottle (not shown) including eluant, such as saline, is then placed in fluid communication with the inlet port 14 and vent port 26. As shown, the vent port 26 and inlet port 14 may comprise needles that puncture and then seal against a diaphragm of the bottle, although other connections are also possible as embodiments are not limited to that which is illustrated in the figures. A shielded, evacuated collection vial (not shown), having a connection similar to that of the eluant bottle, is then connected to the outlet port 30. The negative pressure of the evacuated vial draws eluant from the eluant bottle and through the flow pathway, including the column, to elute daughter radionuclide for delivery through the outlet port and to the shielded, evacuated vial. The vent allows air to enter the eluant bottle through the vent port to prevent negative pressure in the eluant bottle that might otherwise impede the flow of eluant through the flow pathway. After having eluted daughter radionuclide from the column, the shielded, evacuated collection vial is removed from the outlet port of the generator, and a vial containing a preservative (not shown), having a connection similar to that of the eluant bottle and collection vial is inserted onto the outlet port. The radionuclide generator may then be stored until radionuclide is again to be eluted.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the invention. The advantages and objects of the invention are not necessarily encompassed by each embodiment of the invention.

The present invention is further illustrated by the following Examples, which in no way should be construed as further limiting.

EXAMPLES

Example 1

Elution Efficiency Results of Column Assemblies Exceeding Threshold Limits

Production of column assemblies configured as shown in FIG. 1, but with a vented outlet cover having a vent that opens upwardly rather than downwardly (e.g., a column assembly like that of FIG. 1 but with the cap 48 removed), was monitored to identify column assemblies that exceeded an upper threshold radiation limit, as may be associated with a parent radionuclide present in an outlet or inlet line. Radionuclide was eluted from the column assemblies that exceeded the upper threshold limit. Elution efficiency (Tc-99m yield) was then measured for these column assemblies. For some of the column assemblies, residual moisture levels were tested prior to measuring elution efficiency, while for others, elution efficiency was measured without testing residual moisture levels.

Figure 5:
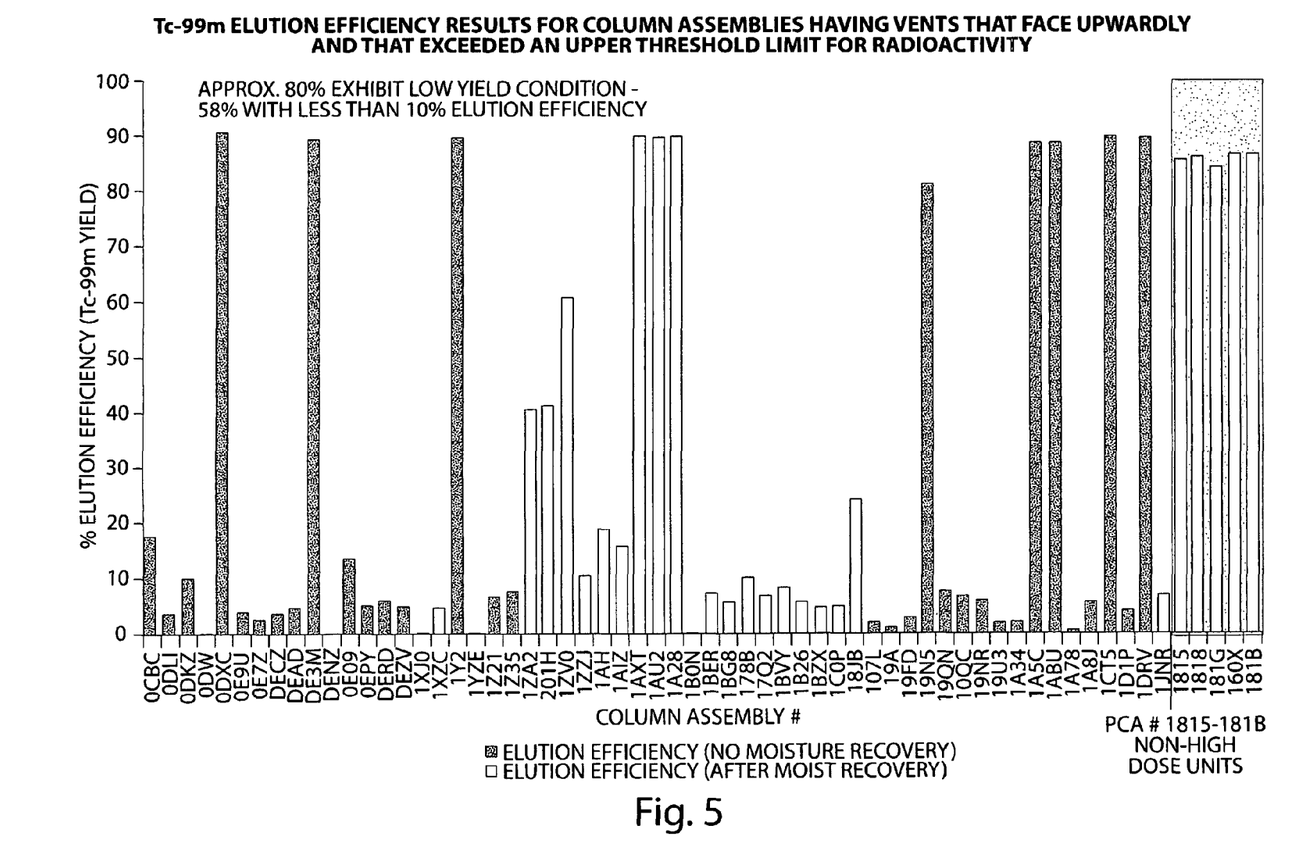
FIG. 5 shows elution efficiencies for column assemblies having a vented outlet cover with a vent that opens upwardly, and that exceeded an upper threshold limit for emitted radiation.

The elution efficiency results for all column assemblies are shown in FIG. 5. The elution efficiency is the ratio of the actual yield of daughter radionuclide to the expected yield of daughter radionuclide, corrected for the elapsed time between elutions. Typically, the Tc-99m elution efficiency is 85%-95%. The Tc-99m yield for the column assemblies that exceeded a threshold limit was impacted for approximately 80% of the column assemblies that were tested for elution efficiency, with 58% of the column assemblies tested exhibiting less than 10% elution efficiency. For comparison, five non-high dose column assemblies (#1815-181B) are also shown in FIG. 5, and have elution efficiency values that exceed 85%. The results of this example suggest a correlation between exceeding upper threshold radiation limits and exhibiting elution efficiency less than 85%.

Example 2

Residual Moisture Recovered from High Dose and Non-High Dose Column Assemblies

Production of column assemblies configured as shown in FIG. 1, but with a vented outlet cover having a vent that opens upwardly rather than downwardly (e.g., a column assembly like that of FIG. 1, but with the cap 48 removed), was monitored to identify column assemblies that exceeded an upper threshold radiation limit, as may be associated with a parent radionuclide present in an outlet or inlet line. Column assemblies that exceeded the upper threshold limit were checked for residual moisture, as were column assemblies that did not exceed the upper threshold limit. Residual moisture was measured using an evacuated vial connected to the outlet port to recover moisture from the fluid path between the inlet port and outlet port, including the column.

Figure 6A:
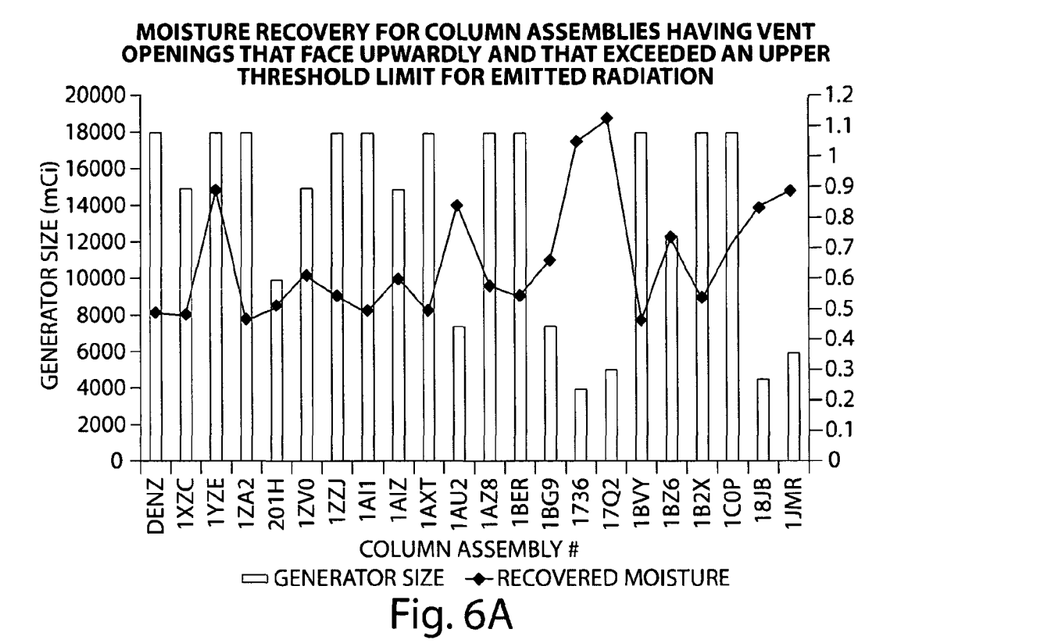
FIGS. 6A and 6B show column assembly residual moisture levels recovered from column assemblies that were found to exceed an upper threshold limit for emitted radiation and for column assemblies that did not exceed the upper threshold limit for emitted radiation.
Figure 6B:
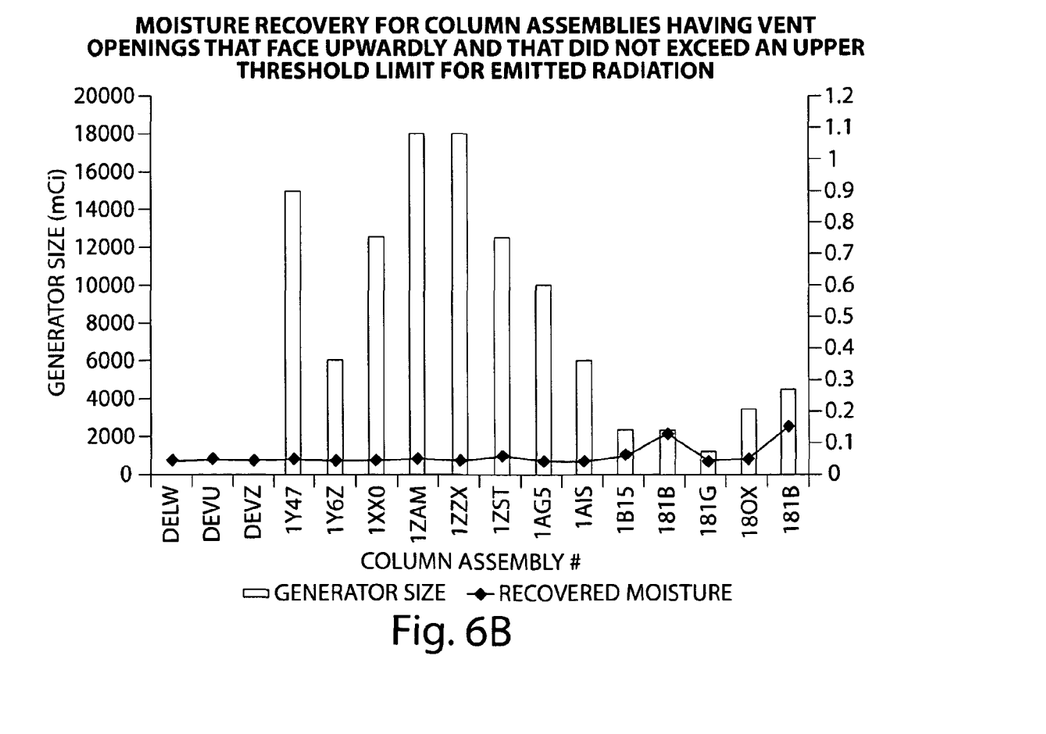

The results, shown in FIGS. 6a and 6b, show that column assemblies found to exceed the upper threshold limit consistently exhibited moisture levels at or in excess of 0.5 grams, while column assemblies that did not exceed the upper limit exhibited moisture levels typically less than 0.05 grams. These results suggest that increased residual moisture in the column assembly may promote the movement of radionuclide to less shielded areas of a column assembly, including the outlet line and/or inlet line, which may result in a column assembly exceeding an upper threshold limit for radiation. Furthermore, excess moisture may reduce elution efficiency (Tc-99m yield) as discussed in Example 1.

Example 3

Figure 7:
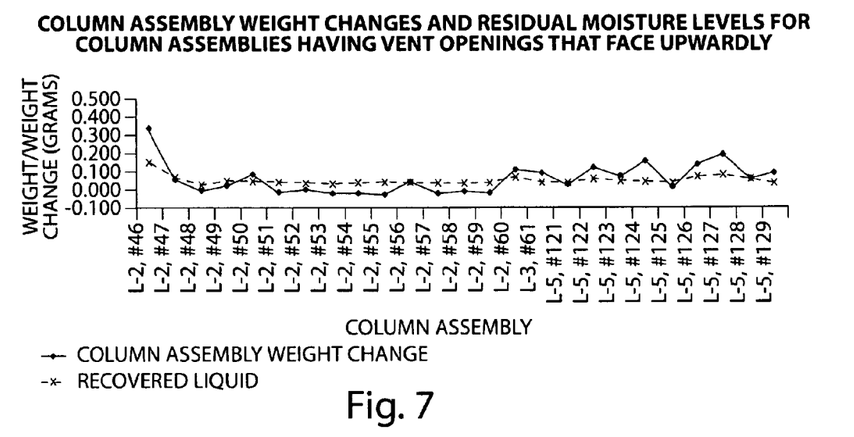
FIG. 7 shows change in column assembly weights during steam sterilization for column assemblies having vent openings oriented upwardly.

Weight Change and Recovered Liquid for Column Assemblies Having Vents Oriented Upwardly and Having Vents Oriented Downwardly Positions were identified within a steam sterilizer where column assemblies having vents oriented upwardly were previously found to have relatively wide range of residual moisture levels following sterilization. Column assemblies configured as shown in FIG. 1, but with a vented outlet cover having a vent that opens upwardly rather than downwardly (e.g., a column assembly like that of FIG. 1, but with the cap 48 removed), were charged with eluant lacking radionuclide. Column assemblies were charged with different amounts of eluant so as to represent different size (i.e., Mo-99 activity levels) of radionuclide generators that are typically produced. The column assemblies were weighed, and placed in the identified positions within the sterilizer for steam sterilization. The column assemblies were subjected to steam sterilization, and then again weighed after sterilization. A change in column assembly weight was calculated. Results of this test are shown in FIG. 7.

Figure 8:
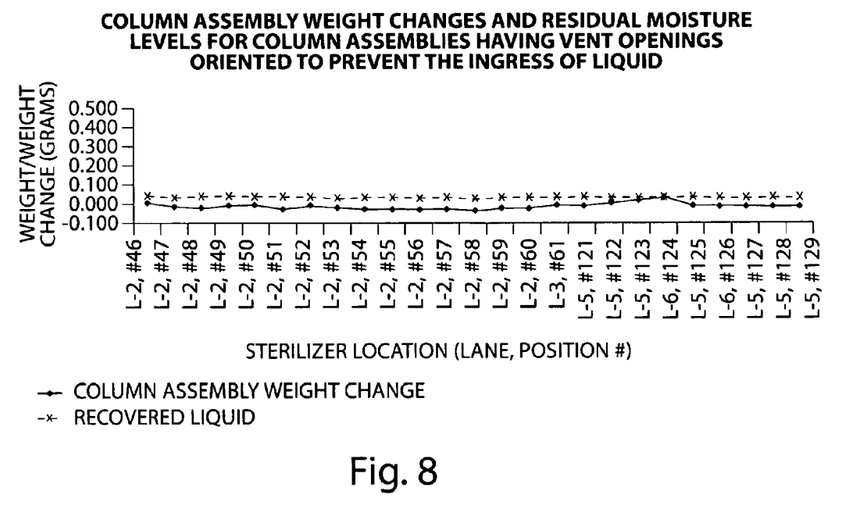
FIG. 8 shows change in column assembly weights during sterilization for column assemblies having vent openings oriented to prevent the ingress of liquid.

The test was then repeated with column assemblies configured as shown in FIG. 1, including a vented outlet cover with a vent that opens downwardly. The results of this test are shown in FIG. 8. The mean recovered liquid from the column assemblies having vents that open downwardly was 0.040 grams, a 25% reduction from the 0.053 grams of the column assemblies having vents that open upwardly. Additionally, the standard deviation of liquid recovered from column assemblies having vents that open downwardly was 0.002 grams, as opposed to 0.024 grams for column assemblies having vents that open upwardly. Similarly, the relative standard deviation of liquid recovered from column assemblies having vents that open downwardly was 5.0%, as opposed to 3% for column assemblies having vents that open upwardly, a reduction of 90.0%.

Example 4

Weight Change and Recovered Liquid for Column Assemblies Having Vents Oriented Upwardly and Having Vents Oriented Downwardly After Two Sterilizations The procedures described above with respect to Example 3 were repeated, except that column assemblies were subjected to two complete steam sterilizations, as may occur in the production of radionuclide generators when a steam sterilization is interrupted, such as due to a power outage, and may need to be repeated.

Figure 9:
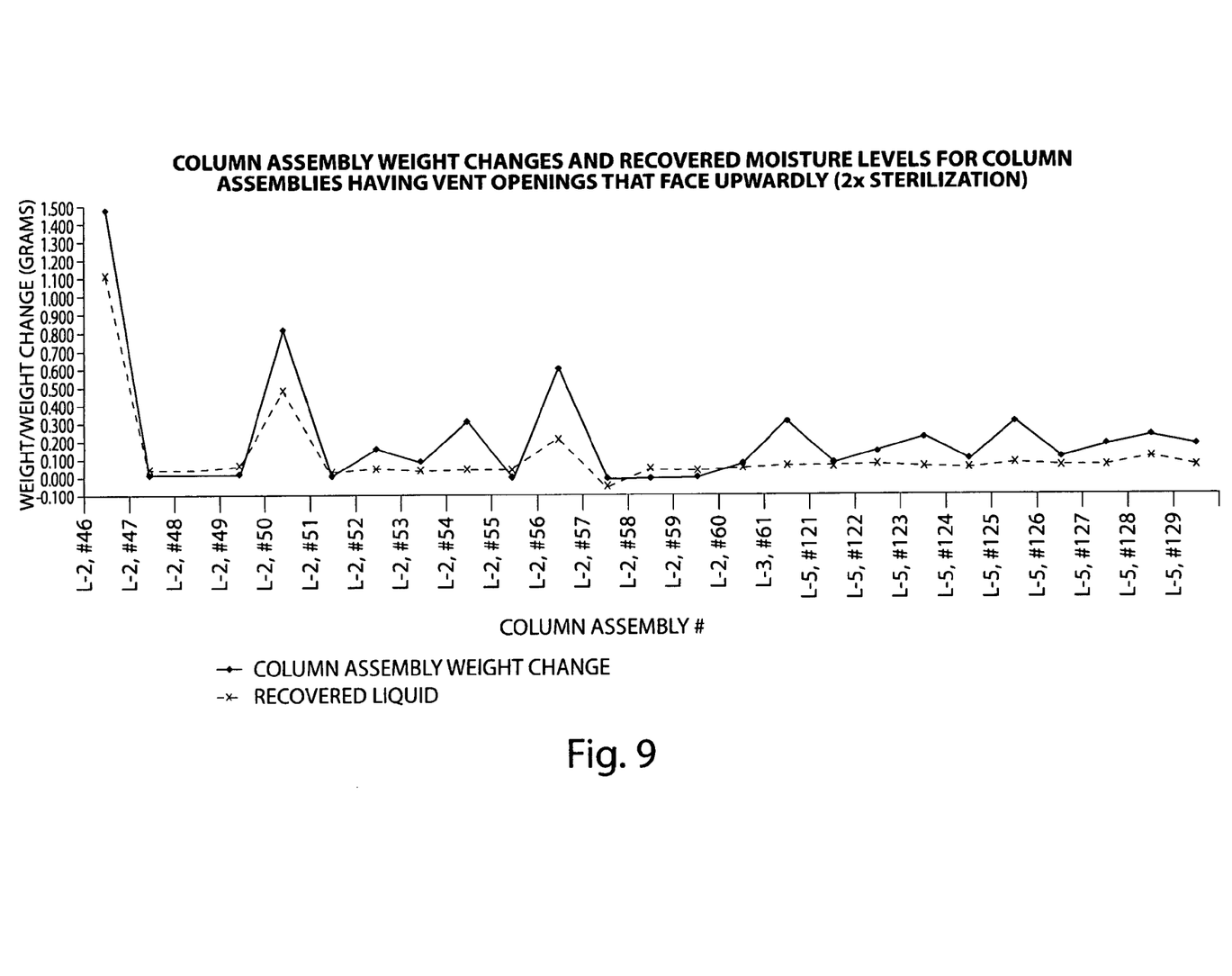
FIG. 9 shows change in column assembly weights during two consecutive steam sterilizations for column assemblies having vent openings oriented upwardly.
Figure 10:
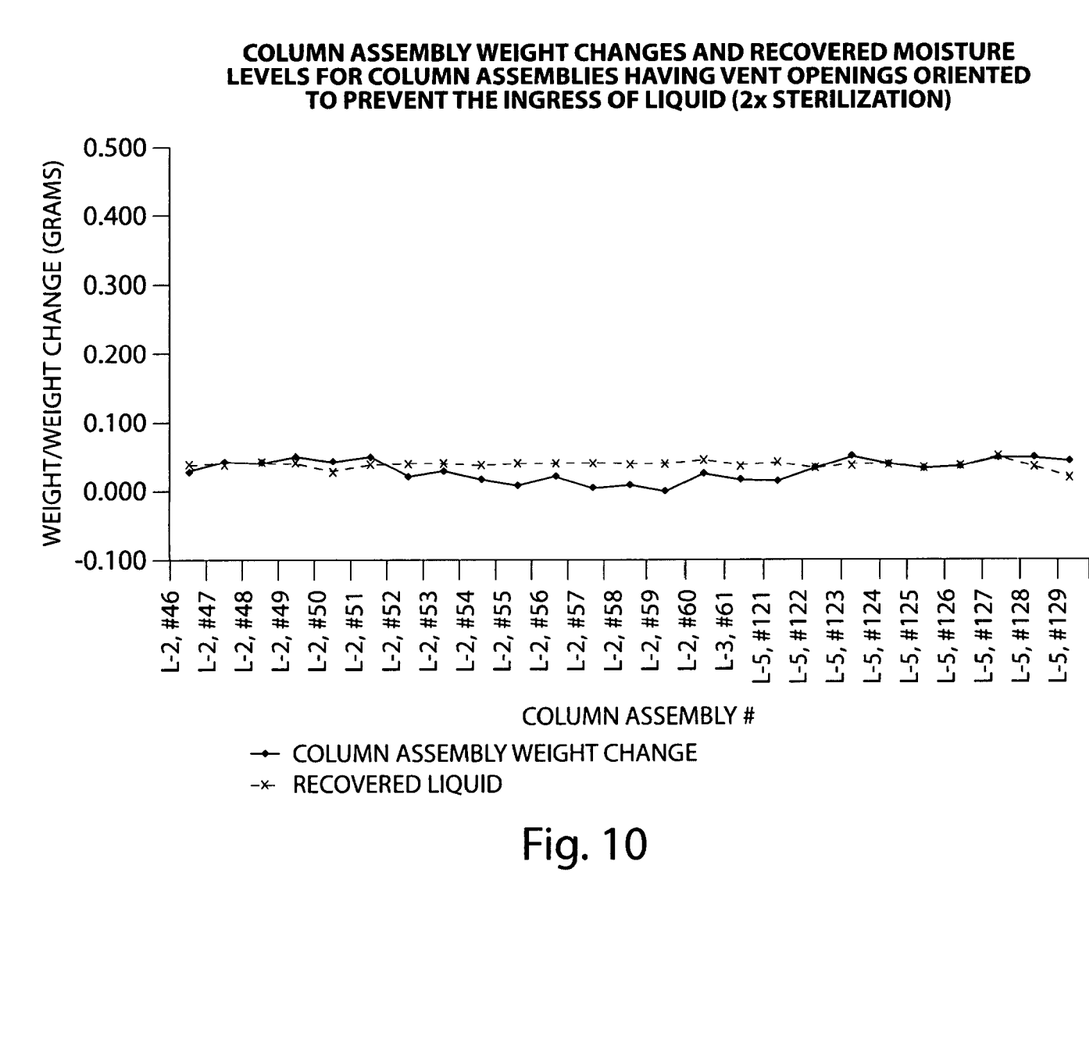
FIG. 10 shows change in column assembly weights during two consecutive steam sterilizations for column assemblies having vent openings oriented to prevent the ingress of liquid.

The results for column assemblies configured as shown in FIG. 1, but with a vented outlet cover having a vent that opens upwardly rather than downwardly, are shown in FIG. 9. The results for column assemblies configured as shown in FIG. 1, including a vented outlet cover with a vent that opens downwardly, are shown in FIG. 10. The mean recovered liquid from the column assemblies having vents that open downwardly was 0.039 grams, a 64% reduction from the 0.108 grams of the column assemblies having vents that open upwardly. Additionally, the standard deviation of liquid recovered from column assemblies having vents that open downwardly was 0.006 grams, as opposed to 0.231 grams for column assemblies having vents that open upwardly. Similarly, the relative standard deviation of liquid recovered from column assemblies having vents that open downwardly was 15.4%, as opposed to 214.0% for column assemblies having vents that open upwardly, a reduction of 92.8%.

This Example suggests that a vented outlet cover with a vent that opens downwardly may prevent the ingress of excess liquid, even after multiple steam sterilizations.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A column assembly of a radionuclide generator, comprising:
   a column having an interior containing a medium for retaining a long-lived parent radionuclide that produces a relatively short-lived daughter radionuclide;
   an inlet port in fluid communication with the interior of the column; and
   an outlet port in fluid communication with the interior of the column;
   wherein the column assembly includes a vent opening that provides fluid access to the interior of the column via the outlet port, the vent opening oriented to face downwardly when the column is positioned below the outlet port during sterilization to prevent condensate from entering the vent opening from above.

2. The column assembly of claim 1, further comprising:
   an outlet cover that at least partially covers the outlet port and that at least partially defines the vent opening.

3. The column assembly of claim 2, wherein the outlet port includes a needle structure and the outlet cover includes a pierceable membrane that receives the needle structure of the outlet port.

4. The column assembly of claim 2, wherein the outlet cover includes a body portion and a removable cap.

5. The column assembly of claim 4, wherein the vent opening is defined as an annular space between the removable cap and the body portion.

6. The column assembly of claim 4, further comprising:
   a filter in the outlet cover.

7. The column assembly of claim 6, wherein the filter is bacteria retentive.

8. The column assembly of claim 6, wherein the filter is positioned at the vent opening.

9. The column assembly of claim 1, further comprising:
   a filter positioned between and in fluid communication with the outlet port and the column.

10. The column assembly of claim 1, wherein the inlet port is accessible from outside of a shielded package that receives the column assembly, when the column is inside of the shielded package.

11. The column assembly of claim 10, in combination with the shielded package.

12. The column assembly of claim 1, further comprising:
    a plug removably attached to the inlet port to block fluid communication to the inlet port from an atmosphere outside of the column assembly.

13. The column assembly of claim 1, wherein the medium includes alumina.

14. The column assembly of claim 1, in combination with the long-lived parent radionuclide and the relatively short-lived daughter radionuclide.

15. The combination of claim 14, wherein the long-lived parent radionuclide includes molybdenum-99 and the relatively short-lived daughter radionuclide includes technetium-99m.

16. A method of producing a terminally sterile column assembly of a radionuclide generator, comprising:
    providing a column assembly of a radionuclide generator that includes:
       a column having a long-lived parent radionuclide that produces a relatively short-lived daughter radionuclide;
       an inlet port in fluid communication with the column; and
       an outlet port in fluid communication with the column, the outlet port includes a vent opening that provides fluid access to the column;
    positioning the column assembly in an orientation with the vent opening facing downwardly to prevent condensate from entering the vent opening from above; and
    exposing the column assembly to steam for sterilization.

17. A column assembly of a radionuclide generator, comprising:
    a column and an outlet port, the column including a medium for retaining a long-lived parent radionuclide that produces a relatively short-lived daughter radionuclide, the outlet port in fluid communication with the column and covered with a vented outlet cover to provide a terminally sterilizable column assembly, the vented outlet cover having a vent opening that provides fluid access to the column and that prevents the ingress of gravity-driven liquid to produce a column assembly that consistently exhibits high yield.

18. A column assembly of a radionuclide generator, comprising:
    a column and an outlet port, the column including a medium for retaining a long-lived parent radionuclide that produces a relatively short-lived daughter radionuclide, the outlet port in fluid communication with the column and covered with a vented outlet cover to provide a terminally sterilizable column assembly, wherein means are provided to prevent the ingress of gravity-driven liquid to produce a column assembly that consistently exhibits high yield and that prevents migration of parent radionuclide away from the column.

19. A column assembly of a radionuclide generator, comprising:
    a column and an outlet port, the column including a medium for retaining a long-lived parent radionuclide that produces a relatively short-lived daughter radionuclide, the outlet port in fluid communication with the column and a means that allows for an exchange of steam while reliably preventing excess liquid from being introduced to portions of the column assembly during sterilization.

20. A column assembly of a radionuclide generator, comprising:
    a column and an outlet port, the column including a medium for retaining a long-lived parent radionuclide that produces a relatively short-lived daughter radionuclide, the outlet port in fluid communication with the column and covered with a vented outlet cover to provide a terminally sterilizable column assembly, the vented outlet cover having a vent opening that provides fluid access to the column and that prevents the ingress of gravity-driven liquid to produce a column assembly that prevents migration of parent radionuclide away from the column.

* * * * *

UNITED STATES PATENT AND TRADEMARK OFFICE
CERTIFICATE OF CORRECTION

PATENT NO. : 8,569,713 B2
APPLICATION NO. : 13/320216
DATED : October 29, 2013
INVENTOR(S) : John Henry Evers Page 1 of 1

It is certified that error appears in the above-identified patent and that said Letters Patent is hereby corrected as shown below:

In the Claims

At column 14, line 6-9, claim 15 should read:

15. The column assembly of claim 14, wherein the long-lived parent radionuclide includes molybdenum-99 and the relatively short-lived daughter radionuclide includes technetium-99m.

Signed and Sealed this
Twenty-fourth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,569,713 B2
APPLICATION NO. : 13/320216
DATED : October 29, 2013
INVENTOR(S) : John Henry Evers

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 49 days.

Signed and Sealed this
Twenty-third Day of May, 2017

Michelle K. Lee
*Director of the United States Patent and Trademark Office*